(12) United States Patent
Gerlitz

(10) Patent No.: US 9,358,402 B2
(45) Date of Patent: Jun. 7, 2016

(54) HANDHELD LOW-LEVEL LASER THERAPY APPARATUS

(71) Applicant: Michael Schlosser, Haifa (IL)

(72) Inventor: Yonatan Gerlitz, Herzliya (IL)

( * ) Notice: Subject to any disclaimer, the term of this patent is extended or adjusted under 35 U.S.C. 154(b) by 0 days.

(21) Appl. No.: 14/341,153

(22) Filed: Jul. 25, 2014

(65) Prior Publication Data

US 2014/0336732 A1 Nov. 13, 2014

Related U.S. Application Data

(63) Continuation of application No. 12/534,878, filed on Aug. 4, 2009, now Pat. No. 8,790,382.

(51) Int. Cl.
| | |
|---|---|
| *A61N 5/06* | (2006.01) |
| *B23K 26/00* | (2014.01) |
| *B23K 26/06* | (2014.01) |

(Continued)

(52) U.S. Cl.
CPC ................ *A61N 5/06* (2013.01); *A61B 18/203* (2013.01); *A61N 5/0616* (2013.01); *B23K 26/0006* (2013.01); *B23K 26/0096* (2013.01); *B23K 26/0648* (2013.01); *B23K 37/006* (2013.01); *A61B 18/20* (2013.01); *A61B 2017/00017* (2013.01); *A61B 2017/00747* (2013.01); *A61B 2018/00452* (2013.01); *A61B 2018/00636* (2013.01); *A61B 2018/00642* (2013.01); *A61B 2018/2025* (2013.01); *A61N 2005/067* (2013.01); *A61N 2005/0626* (2013.01); *A61N 2005/0644* (2013.01); *A61N 2005/0651* (2013.01); *A61N 2005/0659* (2013.01); *B23K 2203/00* (2013.01)

(58) Field of Classification Search
CPC ............... A61B 2005/0644; A61B 2005/0659; A61B 2005/0626; A61B 2005/0651; A61B 2005/067

See application file for complete search history.

(56) References Cited

U.S. PATENT DOCUMENTS

| 4,979,180 A | 12/1990 | Muncheryan |
| 5,147,349 A | 9/1992 | Johnson et al. |

(Continued)

FOREIGN PATENT DOCUMENTS

| JP | H0199576 | 4/1989 |
| JP | 2003066368 | 3/2003 |

(Continued)

OTHER PUBLICATIONS

US Patent and Trademark Office, Non-Final Office Action for U.S. Appl. No. 12/534,878 dated Jul. 12, 2012.

(Continued)

*Primary Examiner* — Yuanda Zhang
*Assistant Examiner* — Michael Carter
(74) *Attorney, Agent, or Firm* — Parsons Behle & Latimer

(57) ABSTRACT

A laser therapy device, including: a laser diode that is adapted to produce a monochromatic laser beam; a lens that is adapted to receive the beam directly from the laser diode and exploit the natural divergence of the laser diode to form an essentially coherent monochromatic, collimated beam; wherein the formed beam is adapted to form on a plane perpendicular to the direction of propagation of the beam an elongated illuminated area in which the length of the illuminated area is at least twice the size of the width of the illuminated area; a controller that is adapted to control activation of the laser diode; an encasement enclosing the laser diode, the lens and the controller; wherein the encasement is adapted to be hand held by the user.

20 Claims, 5 Drawing Sheets

(51) Int. Cl.
  *B23K 37/00* (2006.01)
  *A61B 18/20* (2006.01)
  *A61B 17/00* (2006.01)
  *A61B 18/00* (2006.01)
  *A61N 5/067* (2006.01)

(56) References Cited

U.S. PATENT DOCUMENTS

| | | |
|---|---|---|
| 5,259,380 A | 11/1993 | Mendes et al. |
| 5,272,716 A | 12/1993 | Soltz et al. |
| 5,344,434 A | 9/1994 | Talmore |
| 5,464,436 A | 11/1995 | Smith |
| 5,663,828 A | 9/1997 | Knowles et al. |
| 5,941,837 A | 8/1999 | Amano et al. |
| 6,013,096 A | 1/2000 | Tucek |
| 6,069,748 A | 5/2000 | Bietry |
| 6,108,138 A * | 8/2000 | Ophey et al. .................. 359/711 |
| 6,267,779 B1 | 7/2001 | Gerdes |
| 6,306,160 B1 | 10/2001 | Nidetzky |
| 6,358,272 B1 | 3/2002 | Wilden |
| 6,612,719 B2 * | 9/2003 | Richardson et al. .......... 362/268 |
| 6,746,473 B2 | 6/2004 | Shanks et al. |
| 7,118,563 B2 | 10/2006 | Weckwerth et al. |
| 7,374,569 B2 | 5/2008 | Whatcott et al. |
| 7,465,307 B2 | 12/2008 | Connors et al. |
| 7,479,137 B2 | 1/2009 | Yamazaki |
| 7,524,328 B2 | 4/2009 | Connors et al. |
| 2002/0068926 A1 | 6/2002 | Ota et al. |
| 2002/0173833 A1 | 11/2002 | Korman et al. |
| 2003/0058916 A1 | 3/2003 | Tanaka et al. |
| 2003/0233138 A1 | 12/2003 | Spooner |
| 2004/0158301 A1 | 8/2004 | Tucek et al. |
| 2005/0053106 A1 | 3/2005 | Herron et al. |
| 2005/0131499 A1 | 6/2005 | Shanks et al. |
| 2006/0095099 A1 | 5/2006 | Shanks et al. |
| 2006/0129211 A1 | 6/2006 | Canitano et al. |
| 2006/0206173 A1 | 9/2006 | Gertner et al. |
| 2006/0206176 A1 | 9/2006 | Shanks et al. |
| 2006/0224218 A1 | 10/2006 | Tucek et al. |
| 2007/0121069 A1 | 5/2007 | Andersen et al. |
| 2007/0185552 A1 | 8/2007 | Masotti et al. |
| 2007/0198004 A1 | 8/2007 | Altshuler et al. |
| 2008/0027518 A1 | 1/2008 | Island et al. |
| 2008/0058783 A1 | 3/2008 | Altshuler et al. |
| 2008/0077198 A1 * | 3/2008 | Webb et al. ..................... 607/88 |
| 2008/0091179 A1 | 4/2008 | Durkin et al. |
| 2008/0091249 A1 * | 4/2008 | Wang ............................. 607/88 |
| 2008/0125835 A1 * | 5/2008 | Laurent .......................... 607/89 |
| 2008/0310166 A1 | 12/2008 | Chinniah et al. |
| 2009/0073824 A1 | 3/2009 | Kurozuka et al. |
| 2009/0105791 A1 | 4/2009 | McGinnis et al. |
| 2010/0053070 A1 | 3/2010 | Tsai et al. |
| 2011/0032960 A1 | 2/2011 | Gerlitz |
| 2013/0041431 A1 | 2/2013 | Gerlitz et al. |
| 2013/0317571 A1 | 11/2013 | Gerlitz |

FOREIGN PATENT DOCUMENTS

| | | |
|---|---|---|
| JP | 2004538108 | 12/2004 |
| JP | 2005518255 | 6/2005 |
| JP | 2006518610 | 8/2006 |

OTHER PUBLICATIONS

US Patent and Trademark Office, Non-Final Office Action for U.S. Appl. No. 12/534,878 dated Feb. 28, 2013.
US Patent and Trademark Office, Non-Final Office Action for U.S. Appl. No. 12/534,878 dated Jun. 17, 2013.
US Patent and Trademark Office, Final Office Action for U.S. Appl. No. 12/534,878 dated Jan. 6, 2014.
Japan Patent Office; Office Action for Japanese Patent Application No. 2012-523429 dated Jan. 13, 2015.
EP Substantive Examination Report for Application No. 10 806 138.3-1652, dated Jan. 29, 2014.

* cited by examiner

HANDHELD LOW-LEVEL LASER THERAPY APPARATUS

RELATED APPLICATION DATA

This application is a continuation of U.S. patent application Ser. No. 12/534,878, filed on Aug. 4, 2009, and titled "Handheld Low-Level Laser Therapy Apparatus," which is incorporated herein by reference.

FIELD OF THE INVENTION

The present invention relates generally to a handheld low energy laser device for treating people and animals.

BACKGROUND OF THE INVENTION

The use of light for treating people and animals is well known. Since the early history of mankind people have used the light, from the sun to help cure ailments. In the mid 20Th century attempts were made to use concentrated light for treating wounded soldiers in World War II. In later years, the laser, which is based on the quantum phenomenon of stimulated emission, provided an excellent source of concentrated light for treating patients. The laser allows the use of a selected intensity of a monochromatic, and essentially coherent. This has been found to be effective in treating people for various ailments.

The use of a carefully selected wavelength, coherently directed toward a person provides energy for selectively stimulating processes in-living cells. This can help increase blood flow; excite cell activity and intensify inter-cell communications. Laser light treatments have been applied to various ailments such as:

a. Various skeletal and tissue pains and injuries:
1. Rheumatic and/or chronic joint inflammation;
2. Sport injuries, wounds, and fresh scars;
3. Lower and upper back pain; neck pains:
4. Plantar fasciitis and sprains;
5. Tennis elbow;
6. Achilles tendon infection;
7. Carpal tunnel syndrome:
8. Lymphedema—Edema;
b. Medical dermatology:
1. Acne;
2. Burns;
3. Scars;
4. Hemorrhoids;
5. Vitiligo (e.g. discolored skin);
6. Herpes simplex;
c. Aesthetics:
1. Aging and dermatolysis of the face;
2. Wrinkles;
3. Sensitive skin;
4. Post pregnancy stretch marks;
d. dental applications;
e. veterinary applications;
f. Acupuncture treatments;
and other applications.

The use of laser light in therapy has been shown to reduce pain, induce anti-inflammatory activity, induce healing processes and induce skin reuvenation.

In the past light therapy has been applied by large, expensive and hazardous equipment which requires application by trained personnel. Thus miniature, user safelaser therapy devices, which can be used at home, are desirous.

SUMMARY OF THE INVENTION

An aspect of an embodiment of the invention, relates to an apparatus and method for treating people using a handheld low level laser therapy device. The device includes a laser diode that provides a monochromatic single phased laser beam that disperses with a small angle (e.g. between 5-7 degrees) in one direction) and with a larger angle (e.g. between 30-40 degrees) in the direction perpendicular to the first direction. The device exploits the natural divergence of the laser diode to produce a light beam that illuminate a larger area simultaneously with a monochromatic, essentially coherent and collimated light beam.

The device includes a lens that turns the laser beam into a collimated beam wherein the rays from the smaller dispersion angle provides a narrow illumination area and the rays from the larger dispersion angle provide an elongated illumination area. Optionally, the elongated illumination area is at least twice the size of the narrow illumination area. In some embodiments of the invention the illumination area forms a rectangular area. Alternatively, the illumination area is an ellipsoidal area. Optionally, the beam provides eye safety as a result of the dispersion, which provides less intensity per unit area.

In some embodiments of the invention, the monochromatic laser beam is an invisible infrared beam. Optionally, the wavelength of the laser beam is between 800 to 900 nm. In an exemplary embodiment of the invention, a visible light source (e.g. a LED) is used to provide a supplementary visible light beam to accompany the invisible light beam so that a user will be able to see that the device is active and will not point the device toward his eyes. In some embodiments of the invention, the visible light beam coincides with the invisible laser beam. Alternatively, the visible light beam illuminates an area that surrounds the laser beam forming a frame around the invisible laser beam to enhance user safety.

In some embodiments of the invention, the device is activated by an eye safely mechanism that is activated by pressing the light emitting end against the target that is to be illuminated, to prevent a user from shining the laser beam without precaution. Alternatively, or additionally, other activation switches are available on the device.

In some embodiments of the invention, the laser diode is activated non-continuously when the device is activated, for example with a duty cycle of 50% or less. Optionally, the output power of the laser diode is continuously controlled by a servo loop that monitors the output of the laser diode and updates its duty cycle to maintain a constant power output by the laser beam, for example the pulse length or the frequency of turning on the laser diode are updated responsive to the detected intensity.

There is thus provided according to an exemplary embodiment of the invention, a laser therapy device, comprising:
a laser diode that is adapted to produce a monochromatic laser beam;
a lens that is adapted to receive the beam directly from the laser diode and exploit the natural divergence of the laser diode to form an essentially coherent monochromatic, collimated beam; wherein the formed beam is adapted to form on a plane perpendicular to the direction of propagation of the beam an elongated illuminated area in which the length of the illuminated area is at least twice the size of the width of the illuminated area:
a controller that is adapted to control activation of the laser diode; and an encasement enclosing the laser diode, the lens and the controller; wherein the encasement is adapted to be hand held by the user.

In some embodiments of the invention, the lens is a toroidal lens having a different lens radius in the direction producing the length of the illuminated area and the direction producing the width of the illuminated area. Optionally, the beam produced by the laser diode is an infrared laser beam.

In an exemplary embodiment of the invention, the laser therapy device includes a visible light source that produces a visible light beam that is combined with the laser beam to provide a visible light as an indication of the presence of the invisible laser beam. Optionally, the visible light source is mounted, so that the image of the light source is in the focal plane of the lens. In an exemplary embodiment of the invention, the visible light beam is adapted to surround the invisible laser beam forming a frame enclosing the invisible light beam.

In an exemplary embodiment of the invention, the controller is adapted to control the duty cycle of the laser diode. Optionally, the controller is adapted to update the duty cycle of the laser diode to maintain a constant power output although the intensity of the laser diode changes over time. In an exemplary embodiment of the invention, the duty cycle of the beam produced by the laser diode is initially less than 50%. Optionally, the device includes a safety mechanism that activates the device by pressing the device against the illuminated object. In an exemplary embodiment of the invention, the illuminated area forms a rectangular or ellipsoidal shaped area. Optionally, the beam formed is an eye safe beam.

There is further provided according to an exemplary embodiment of the invention, a laser therapy device, comprising:

a laser diode that is adapted to produce a monochromatic laser beam;

a lens that is adapted to receive the beam from the laser diode;

a controller that is adapted to control the duty cycle of the laser diode and maintain a constant power output; and an encasement enclosing the laser diode, the lens and the controller; wherein the encasement is adapted to be hand held by the user.

There is further provided according to an exemplary embodiment of the invention, a laser therapy device, comprising:

a laser diode that is adapted to produce a monochromatic laser beam;

a lens that is adapted to receive the beam from the laser diode:

a controller that is adapted to control activation of the laser diode;

an encasement enclosing the laser diode, the lens and the controller; wherein the encasement is adapted to be hand held by the user; and wherein the device is activated by a safety mechanism by pressiug the device against the illuminated object.

There is further provided according to an exemplary embodiment of the invention, a laser therapy device, comprising:

a laser diode that is adapted to produce a monochromatic laser beam;

a visible light source that is adapted to provide a light beam that surrounds the beam formed by the laser diode, forming a frame around the illumination pattern formed by the laser beam;

a lens that is adapted to receive the beam from the laser diode;

a controller that is adapted to control activation of the laser diode;

an encasement enclosing the laser diode, the lens and the controller; wherein the encasement is adapted to be hand held by the user.

BRIEF DESCRIPTION OF THE DRAWINGS

The present invention will be understood and better appreciated from the following detailed description taken in conjunction with the drawings. Identical structures, elements or parts, which appear in more than one figure, are generally labeled with the same or similar number in all the figures in which they appear, wherein.

DETAILED DESCRIPTION

Figure 1:
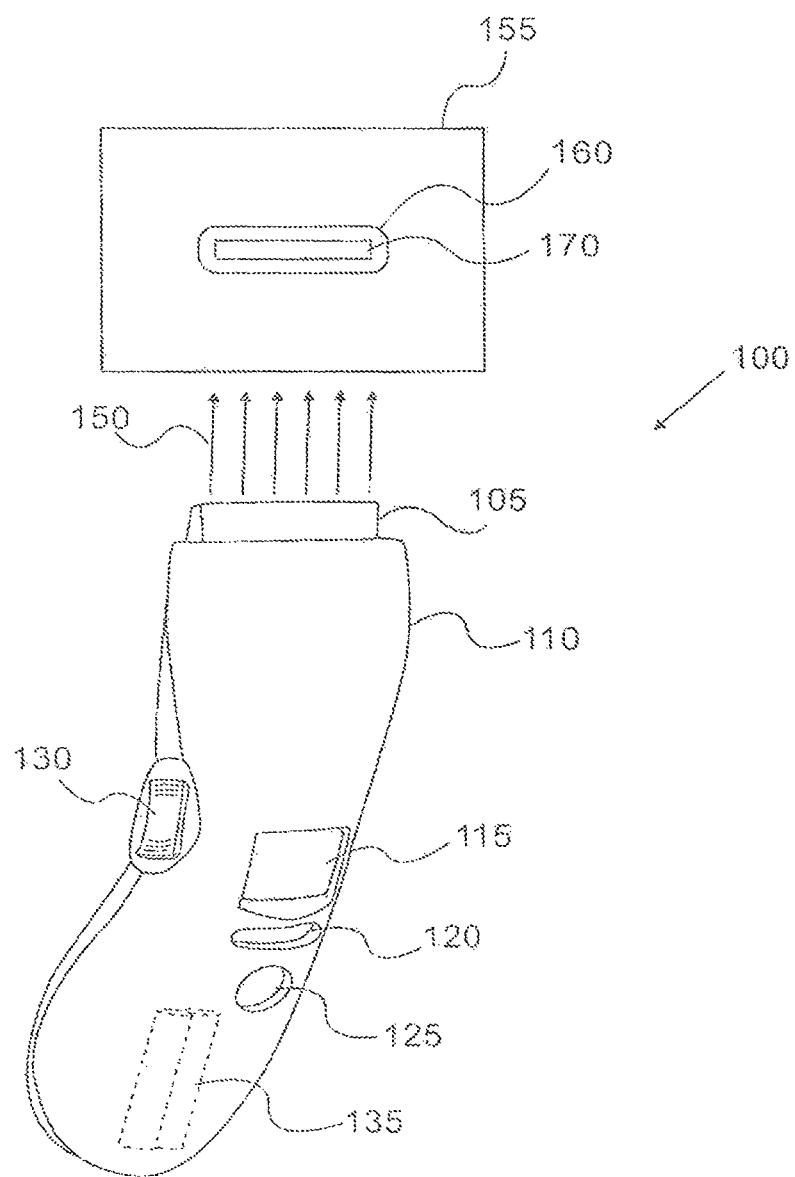
FIG. 1 is a schematic illustration of a handheld low-level laser therapy (LLLT) device for performing laser therapy, according to an exemplary embodiment of the invention.

FIG. 1 is a schematic illustration of a handheld low-level laser therapy (LLLT) device 100 for performing laser therapy, according to an exemplary embodiment of the invention. In an exemplary embodiment of the invention, device 100 provides as output an elongated monochromatic coherent laser beam 170 that is collimated by a lens directly from the natural divergence of a laser diode embedded in device 100. In contrast to prior art devices, instead of focusing the laser beam from the laser diode to a single spot to have a stronger illumination on a single spot, the natural tendency of the laser diode is exploited to form an elongated beam to cover a larger area. The standard laser diode typically has a divergence of about 5-7 degrees along its width and about 30 to 40 degrees along its length. Instead of using a lens to correct the beam to a narrow beam, device 100 uses a lens to form a collimated elongated beam to cover a larger area, for example an area of 3-6 cm by 0.5 to 1 cm. In an exemplary embodiment of the invention, the length of the illuminated area is at least twice the width of the illuminated area. In an exemplary embodiment of the invention, the resulting elongated beam is essentially coherent having a light beam with an essentially common phase as accepted for laser diode emission.

Optionally, by illuminating a large area each point is illuminated with a weaker and safer laser beam, for example an eye safe beam, having an intensity, which is not hazardous to a persons eye. More power can be delivered more accurately to a specific area by illuminating for a longer time or increasing the intensity of the laser diode without moving device 100. In contrast in a single spot laser a single point is illuminated intensely and an area is processed by moving the beam across the user's skin and illuminating each point.

In an exemplary embodiment of the invention, the light sources and electronic circuitry for powering device 100 are encased in an ergonomic encasement 110 designed to fit into a user's hand. Optionally, device 100 includes an on/off switch 125, which turns device 100 on and off. When device 100 is in the on state—it may be activated by pressing on an activation switch 130 located on the side of encasement 110. Alternatively or additionally, device 100 may be activated by pushing eye safety activation switches 105 against the person or object being radiated, when using device 100. Activation when pressing against the person being radiated increase the safety of device 100 since it will not accidentally allow a user to shine light into the user's eye. In some cases pressing against the user's skin is advantageous since it may reduce blood flow and enhance efficiency of the light absorption. Alternatively, in some cases the user may have a wound and it is preferable to not press against the user's skin.

In some embodiments of the invention, device 100 is powered by an internal power source (e.g. batteries 135). Alternatively or additionally, device 100 can be powered by an external power source via a power-cable (not shown) that is plugged into an external power source, such as a household power socket. Optionally, when the device is plugged into an external power source the batteries may be recharged.

In some embodiments of the invention, device 100 includes a display 115, for example an LCD display, which shows various information, such as the status of the battery, and/or a timer/counter. In an exemplary embodiment of the invention, the timer on display 115 is set by the user to a pre-selected value using a selector 120, the value may represent an amount of time in seconds during which the device will remain active when activated by the user. The device will count down and deactivate the device automatically once it counts the pre-selected amount of time. For example if the user whistles to illuminate an area for a specific amount of time, he sets the timer with the desired amount of time and activates device 100. Device 100 will illuminate the area until the time runs out.

Figure 2:
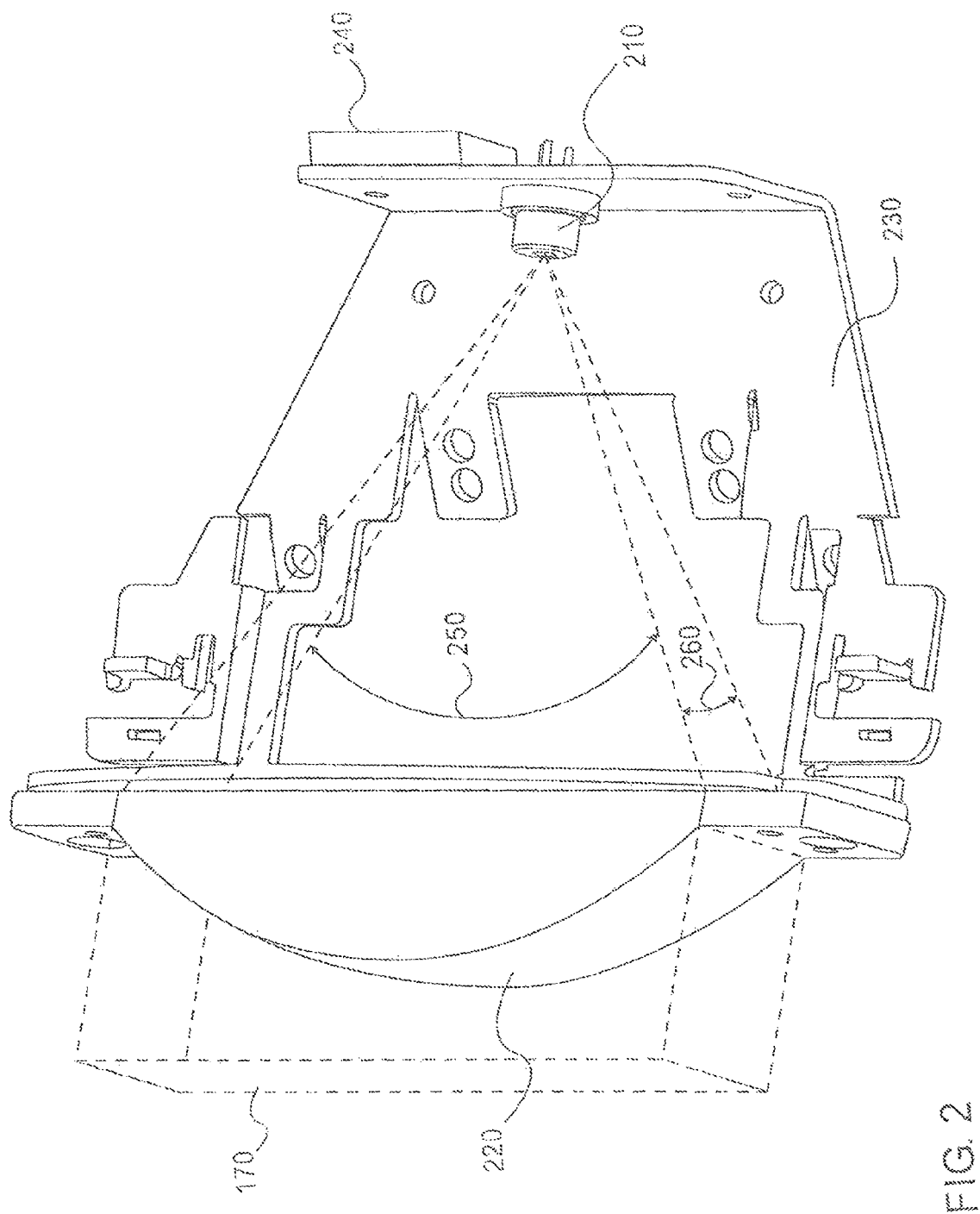
FIG. 2 is a schematic illustration of an internal structure for manufacturing a low-level laser therapy device that demonstrates the use of the natural divergence of the laser diode and lens configuration, according to an exemplary embodiment of the invention.

FIG. 2 is a schematic illustration of an internal structure for manufacturing device 100 that demonstrates the natural divergence of the laser diode and lens configuration, according to an exemplary embodiment of the invention. In an exemplary embodiment of the invention, a laser diode 210 is mounted onto a base 230. In an exemplary embodiment of the invention, laser diode 210 is selected to emit infra-red radiation with a monochromatic wave length between 800-900 nm and a power output of at least 100 mw, so that it will be effective in healing the user. Optionally, the wavelength is selected to have optimal performance in providing power to the biological cells of the user, thus it is possible that other wavelengths may be used (e.g. visible light or ultra-violet light) if found to be more effective in dealing with a specific ailment. Additionally, laser diode 210 may be selected having a stronger or weaker power output.

In an exemplary embodiment of the invention, the light from laser diode 210 disperses with a small angle 260 in one direction, and with a larger angle 250 in the perpendicular direction. Optionally, a lens 220 is placed opposite laser diode 210 to make use of the natural divergence of the laser beam produced by laser diode 210 by collimating the dispersing laser beam and forming an illumination of the elongated monochromatic coherent laser beam 170 on the skin of the user.

In an exemplary embodiment of the invention, lens 220 is a toroidal lens having a different lens radius in two directions, so that the diverging beam formed from laser diode 210 will extend perpendicular to the lens and form an elongated illumination from monochromatic coherent laser beam 170. In some embodiments of the invention, lens 210 has a rectangular or ellipsoidal shape and creates a rectangular or ellipsoidal illumination. Alternatively or additionally, lens 210 may be a single lens, a double lens or any other combination of lenses as long as it produces the elongated monochromatic coherent laser beam 170 to radiate the user. Optionally, elements other than lenses may affect the unity of phase and direction of the coherent laser beam 170.

Figure 3:
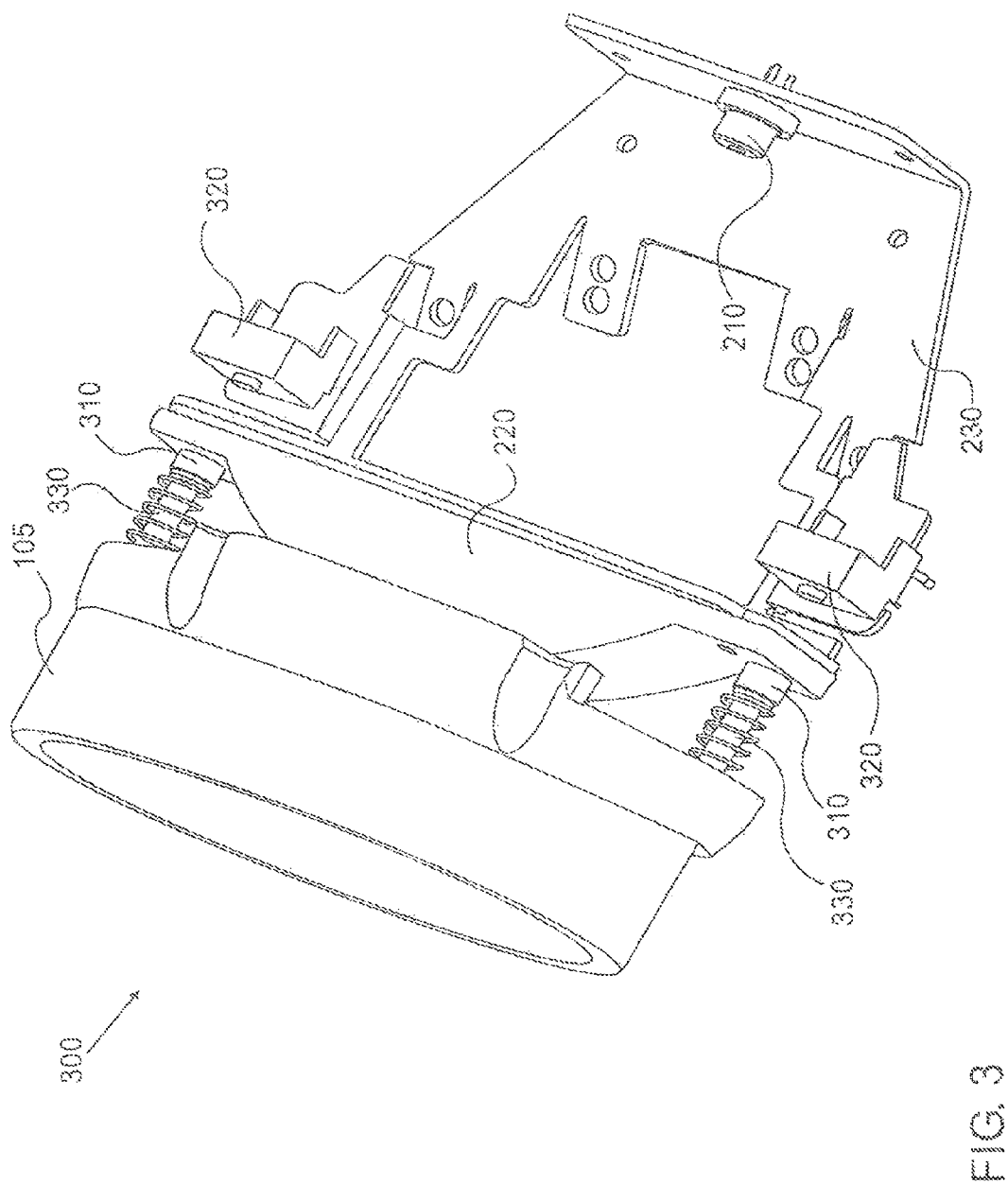
FIG. 3 is a schematic illustration of an internal structure for manufacturing a low-level laser therapy device with a safety activation mechanism, according to an exemplary embodiment of the invention.

FIG. 3 is a schematic illustration of an internal structure for manufacturing device 100 with an eye safety activation mechanism 300, according to an exemplary embodiment of the invention. As mentioned above, in an exemplary embodiment of the invention, when device 100 is turned on, it can be activated by pressing the eye safety activation switch 105 against the body of the user. Optionally, eye safety activation switch 105 is connected to two sliders 310 and 2 springs 330 are inserted on the sliders one for each side. When eye safety activation switch 105 is pushed into encasement 110 sliders 310 are move inward and depress on two micro-switches 320 that instruct controller 240 to activate laser diode 210. The use of eye safety activation switch 105 prevents the user from activating laser diode 210 and aiming it toward his eyes or the eyes of another person.

Figure 4:
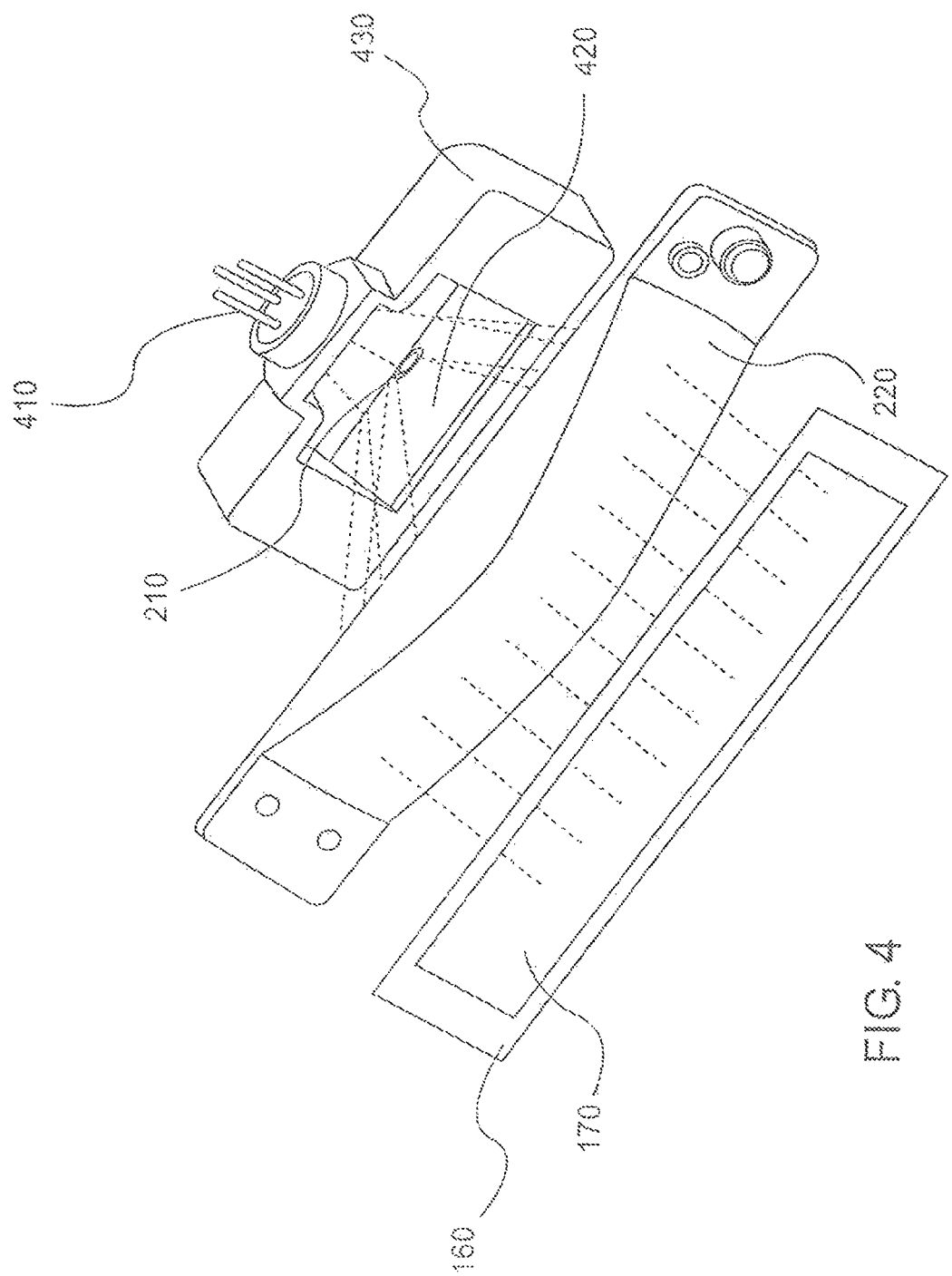
FIG. 4 is a schematic illustration of an internal structure for manufacturing a low-level laser therapy device with a combination mechanism to superimpose visible light beam over laser beam, according to an exemplary embodiment of the invention.

FIG. 4 is a schematic illustration of an internal structure for manufacturing device 100 with a combination mechanism to superimpose visible light beam 160 over laser beam 170, according to an exemplary embodiment of the invention. In an exemplary embodiment of the invention, a visible light source—410 (e.g. a LED) is mounted on a structure 430 above laser diode 210 to provide a visible light source. Optionally, structure 430 includes a polished back surface 420 (e.g. a mirror) to reflect the visible light towards lens 220, so that it will be superimposed over the light rays originating from laser diode 210. In some embodiments of the invention, only specific areas on the back surface are polished to control the resulting geometry of the visible light beam. In an exemplary embodiment of the invention, a cross section of the resulting beam includes an inner area formed by laser beam 170 and a larger area formed by visible light beam 160 that surrounds the inner area and provides a visible border around it, so that the user knows where the invisible laser beam is located.

Optionally, the visible light beam 160 serves as a safety measure, by providing the user with an indication that the invisible laser beam 170 is also there and may be dangerous if aimed at a person's eye.

LED 410 is preferably mounted, so that the image of the light source is in the focus of lens 220.

In an exemplary embodiment of the invention, laser diode 210 is operated in short pulses at a constant frequency, for example of 10-20 μs with a frequency of 250 KHz providing a 25%-50% duty cycle, so that the resulting laser beam will have enough power to penetrate a users skin but the total energy output rate per area is low enough to maintain eye safety if accidentally shined into a persons eyes. In many devices the laser diode 210 is initially provided with a specific power output that deteriorates over time until the laser diode 210 must be replaced (e.g. after 3000-5000 hours of use).

Figure 5:
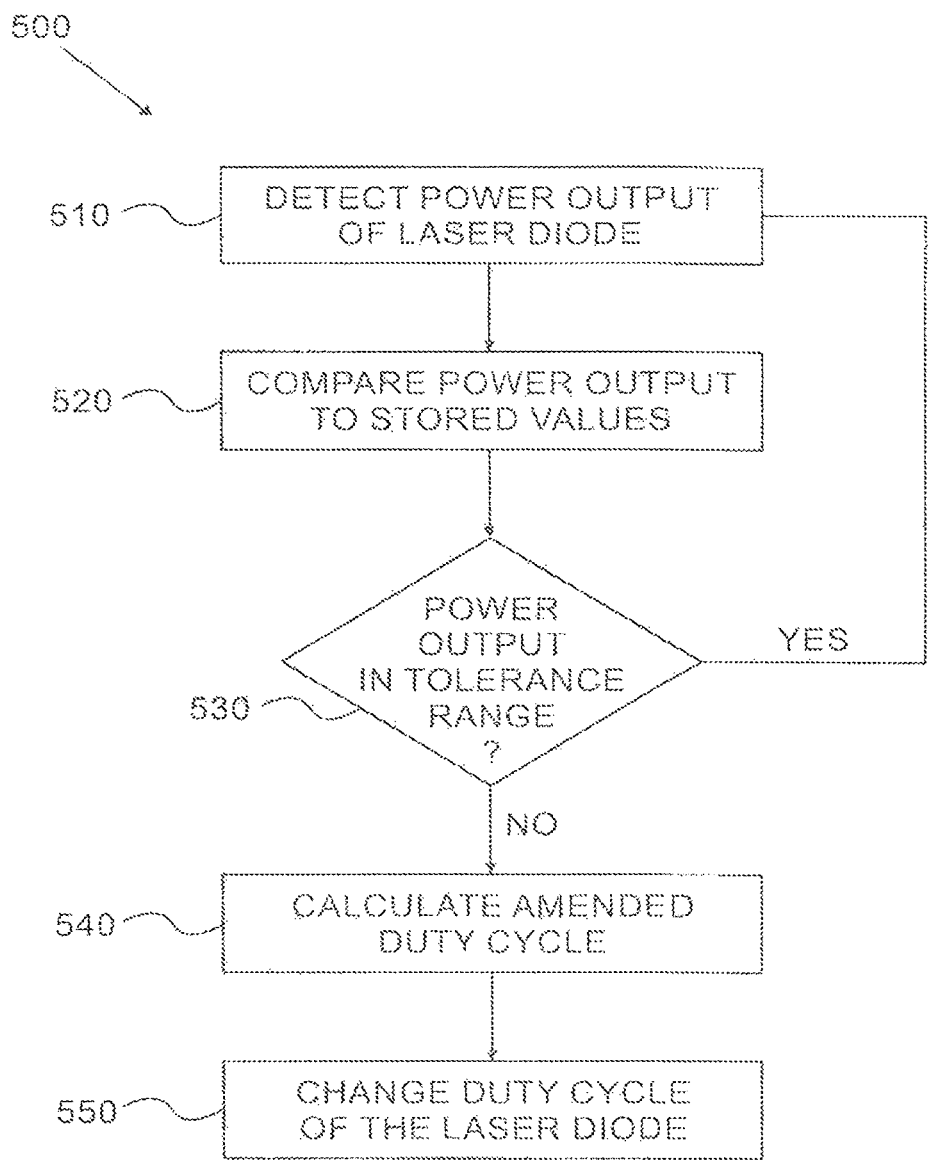
FIG. 5 is a flow diagram of a method of controlling the duty cycle of a laser diode, according to an exemplary embodiment of the invention.

FIG. 5 is a flow diagram 500 of a method of controlling the duty cycle of a laser diode, according to an exemplary embodiment of the invention.

In an exemplary embodiment of the invention, laser diode 210 is controlled by a controller 240 that detects (510) the power output of the laser diode. Optionally, controller 240 compares the power output to a stored value to determine if the power output is within a tolerance range (530) or if laser diode 210 has become weaker and is underperforming.

If the power output is within the tolerance range then the controller continues to periodically monitor the power output of laser diode 210. Otherwise controller 240 calculates (540) an amended duty cycle that will provide the desired power output, for example by increasing the pulse length or by raising the activation frequency of laser diode 210. Controller 240 changes (550) the duty cycle, so that device 100 maintains a constant power output. Optionally, controlling the duty cycle enables prolonging the lifetime of using device 100 without replacing laser diode 210, although the intensity of laser diode 210 deteriorates over time. Optionally, the duty cycle may vary from less than 50% to more than 70%, for example from 10% to 100% to maintain a constant power output.

In an exemplary embodiment of the invention, a stronger laser diode (e.g. 100-900 mw) is used while providing the same power output as generated by a weaker laser diode (e.g. less than 100 mw) that is continuously on (100% duty cycle). As a result the laser beam is safer even though it is more intense since the beam is on intermittently and the target can cool off between pulses. When applying the beam to a user's skin the same overall power is delivered over the same amount of time.

Based on the above description it should be noted that device 100 includes a number of features that enhance user safety and/or enhance clinical efficiency:

1. A visible indication surrounding the laser beam to provide indication of the position of the laser beam;
2. A stronger laser beam with a controlled pulse length and duty cycle to prevent eye damage, since the beam is active only for a short period of time in every second;
3. A laser beam that is dispersed over a wide area to enable treating larger areas simultaneously with an eye safety light beam;
4. A secure activation switch that is only activated when pressing it against the target area.

It should be appreciated that the above described methods and apparatus may be varied in many ways, including omitting or adding steps, changing the order of steps and the type of devices used. It should be appreciated that different features may be combined in different ways. In particular, not all the features shown above in a particular embodiment are necessary in every embodiment of the invention. Further combinations of the above features are also considered to be within the scope of some embodiments of the invention.

It will be appreciated by persons skilled in the art that the present invention is not limited to what has been particularly shown and described hereinabove. Rather the scope of the present invention is defined only by the claims, which follow.

I claim:

1. A laser therapy device, comprising:
    a laser diode that is adapted to produce a monochromatic laser beam that naturally diverges in two orthogonal directions;
    a lens that is adapted to receive the beam directly from the laser diode and to exploit the natural divergence of the laser diode in two orthogonal directions to form an essentially coherent monochromatic, collimated beam in the two orthogonal directions as output from the lens; the formed beam being adapted to form on a plane perpendicular to the direction of propagation of the beam an elongated illuminated area in which the length of the illuminated area is at least twice the size of the width of the illuminated area as a result of collimating the beam while exploiting the natural divergence of the laser diode;
    a controller that is adapted to control activation of the laser diode, the controller being configured to increase a duty cycle of the laser diode to maintain a constant power output although the intensity of the laser diode changes over time as a result of performance deterioration, the configuration including controller settings that automatically;
        detect a power output of the laser diode;
        compare the power output to stored values;
        determine power output is weaker and underperforming;
        calculate an amended duty cycle; and
        increase the duty cycle of the laser diode to the amended duty cycle;
    an encasement enclosing said laser diode, said lens and said controller; wherein said encasement is adapted to be hand held by the user; and
    the laser therapy device being configured to irradiate a surface outside of the encasement with the formed beam without further modification of the formed beam.

2. A laser therapy device according to claim 1, wherein said lens is a toroidal lens having a different lens radius in the direction producing the length of the illuminated area and the direction producing the width of the illuminated area;
    wherein the radius in both directions is selected to provide as output a collimated beam in the two orthogonal directions resulting from the natural divergence of the laser diode.

3. A laser therapy device according to claim 1, wherein the beam produced by said laser diode exhibits a wavelength between 800-900 nm as an infrared laser beam.

4. A laser therapy device according to claim 3, further comprising a visible light source configured to produce a visible light beam that is combined with the laser beam to provide a visible light as an indication of the presence of the infrared laser beam, the visible light source being mounted so that the image of the light source is in the focal plane of the lens.

5. A laser therapy device according to claim 3, wherein the laser diode exhibits a power output of 100-900 mW.

6. A laser therapy device according to claim 5, wherein the controller is configured to produce a pulse length of 10-20 µs.

7. A laser therapy device according to claim 6, wherein the beam formed is configured to enhance user safety compared to a beam formed by a same laser therapy device that does not control pulse length to 10-20 µs.

8. A laser therapy device according to claim 1, wherein the controller settings are implemented in a servo loop.

9. A laser therapy device according to claim 1, wherein the duty cycle of the beam produced by the laser diode is initially less than 50% and the amended duty cycle is greater than 50%.

10. A laser therapy device according to claim 1, wherein the illuminated area forms a rectangular or ellipsoidal shaped area.

11. A laser therapy device according to claim 1, wherein the laser therapy device is configured to irradiate the surface with the formed beam directly from the lens.

12. A laser therapy device, comprising:
    a laser diode that is adapted to produce a monochromatic laser beam that naturally diverges in two orthogonal directions, the beam produced by said laser diode exhibiting a wavelength between 800-900 nm as an infrared laser beam;

a lens that is adapted to receive the beam directly from the laser diode and to exploit the natural divergence of the laser diode in two orthogonal directions to form an essentially coherent monochromatic, collimated beam in the two orthogonal directions as output from the lens; the formed beam being adapted to form on a plane perpendicular to the direction of propagation of the beam an elongated illuminated area in which the length of the illuminated area is at least twice the size of the width of the illuminated area as a result of collimating the beam while exploiting the natural divergence of the laser diode;

a controller that is adapted to control activation of the laser diode;

an encasement enclosing said laser diode, said lens and said controller; wherein said encasement is adapted to be hand held by the user; and the laser therapy device being configured to irradiate a surface outside of the encasement with the formed beam without further modification of the formed beam;

a visible light source configured to produce a visible light beam that is combined with the laser beam to provide a visible light as an indication of the presence of the infrared laser beam, the visible light source being mounted so that the image of the light source is in the focal plane of the lens.

13. A laser therapy device according to claim 12, wherein the device is configured to produce the visible light beam to surround the infrared laser beam forming a frame enclosing the infrared laser beam.

14. A laser therapy device, comprising:

a laser diode that exhibits a power output of 100-900 mW and is adapted to produce a monochromatic laser beam with a wavelength between 800-900 nm as an infrared laser beam that naturally diverges in two orthogonal directions;

a toroidal lens that is adapted to receive the beam directly from the laser diode and to exploit the natural divergence of the laser diode in two orthogonal directions to form an essentially coherent monochromatic, collimated beam in the two orthogonal directions as output from the lens; the formed beam being adapted to form on a plane perpendicular to the direction of propagation of the beam an elongated illuminated area in which the length of the illuminated area is at least twice the size of the width of the illuminated area as a result of collimating the beam while exploiting the natural divergence of the laser diode;

a controller that is adapted to control activation of the laser diode and to update a duty cycle of the laser diode to maintain a constant power output although the intensity of the laser diode changes over time as a result of performance deterioration; and an encasement enclosing said laser diode, said lens and said controller; wherein said encasement is adapted to be hand held by the user; and a safety mechanism configured to activate the device when pressing the device against the illuminated object.

15. A laser therapy device according to claim 14, wherein the laser therapy device is configured to irradiate the surface with the formed beam directly from the lens.

16. A laser therapy device according to claim 14, further comprising a visible light source configured to produce a visible light beam combined with the laser beam to provide an indication of the presence of the infrared laser beam, the laser therapy device being configured to produce the visible light beam to surround the infrared laser beam forming a frame enclosing the infrared laser beam.

17. A laser therapy device according to claim 14, wherein the safety mechanism comprises a microswitch within the encasement and a slider configured to depress the microswitch in turn configured to instruct the controller to activate the laser diode.

18. A method of using a low-level laser therapy device, comprising:

using a laser diode that exhibits a power output of 100-900 mW and producing a monochromatic laser beam with a wavelength between 800-900 nm as an infrared laser beam that naturally diverges in two orthogonal directions;

using a lens and receiving the beam directly from the laser diode and exploiting the natural divergence of the laser diode in two orthogonal directions and forming an essentially coherent monochromatic, collimated beam in the two orthogonal directions as output from the lens; the formed beam forming on a plane perpendicular to the direction of propagation of the beam an elongated illuminated area in which the length of the illuminated area is at least twice the size of the width of the illuminated area as a result of collimating the beam while exploiting the natural divergence of the laser diode, the illuminated area forming a rectangular or ellipsoidal shaped area;

using a controller and controlling activation of the laser diode to produce a pulse length of 10-20 μs;

using an encasement and enclosing said laser diode, said lens and said controller; wherein said encasement is hand held by the user; and the laser therapy device irradiating a surface outside of the encasement with the formed beam without further modification of the formed beam, the formed beam enhancing user safety compared to a beam formed by a same low-level laser therapy device that does not control pulse length to 10-20 μs.

19. A laser therapy method according to claim 18, further comprising the laser therapy device irradiating the surface with the formed beam directly from the lens.

20. A laser therapy method according to claim 19, wherein the illuminated area has dimensions of 3 to 6 cm by 0.5 to 1 cm.

* * * * *